US006561983B2

United States Patent
Cronin et al.

(10) Patent No.: US 6,561,983 B2
(45) Date of Patent: May 13, 2003

(54) ATTACHMENTS OF COMPONENTS OF ULTRASONIC BLADES OR WAVEGUIDES

(75) Inventors: Michael D. Cronin, Cincinnati, OH (US); Jean M. Beaupre, Blue Ash, OH (US); Lee E. Reichel, Springboro, OH (US); Jonathan E. Tuttle, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 44 days.

(21) Appl. No.: 09/774,908

(22) Filed: Jan. 31, 2001

(65) Prior Publication Data

US 2002/0103438 A1 Aug. 1, 2002

(51) Int. Cl.[7] .............................................. A61B 8/00
(52) U.S. Cl. ......................... 600/461; 29/446; 29/450; 29/451; 403/278; 403/279; 403/282
(58) Field of Search ................................ 600/437–472; 403/278, 279, 282, 305; 29/446, 450, 451, 455.1

(56) References Cited

U.S. PATENT DOCUMENTS

| | | | |
|---|---|---|---|
| 4,590,655 A | | 5/1986 | Javorik |
| 5,057,119 A | | 10/1991 | Clark et al. |
| 5,059,210 A | | 10/1991 | Clark et al. |
| 5,167,725 A | | 12/1992 | Clark et al. |
| 5,284,148 A | * | 2/1994 | Dias et al. .................. 600/459 |
| 5,322,055 A | | 6/1994 | Davison et al. |
| 5,324,299 A | | 6/1994 | Davison et al. |
| 5,443,240 A | | 8/1995 | Cunningham |
| 5,449,370 A | | 9/1995 | Vaitekunas |
| 5,488,955 A | * | 2/1996 | Dias .......................... 600/459 |
| 5,630,420 A | | 5/1997 | Vaitekunas |
| 5,746,756 A | | 5/1998 | Bromfield et al. |
| 5,797,848 A | * | 8/1998 | Marian et al. .............. 600/454 |
| 5,848,546 A | | 12/1998 | Allison et al. |
| 5,993,447 A | | 11/1999 | Blewett et al. |
| 5,993,458 A | | 11/1999 | Vaitekunas et al. |
| 6,004,335 A | | 12/1999 | Vaitekunas et al. |
| 6,051,010 A | | 4/2000 | DiMatteo et al. |
| 6,063,098 A | | 5/2000 | Houser et al. |
| 6,206,844 B1 | | 3/2001 | Reichel et al. |

FOREIGN PATENT DOCUMENTS

| | | |
|---|---|---|
| EP | 0891744 A1 | 1/1999 |
| JP | 61-152959 | 7/1986 |
| JP | 10-71439 | 3/1998 |
| WO | WO 99/19017 | 4/1999 |

* cited by examiner

Primary Examiner—George Manuel
Assistant Examiner—William C Jung
(74) Attorney, Agent, or Firm—Verne E. Kreger, Jr.

(57) ABSTRACT

A connection union and method for securing together first and second components of an ultrasonic waveguide or blade. The first and second components of the ultrasonic waveguide or blade are formed as complementary components which engage each other with a complementary fitting. Then a compressed fit over the connection union is formed by an electromagnetic metal forming operation which compressively deforms a female coupling member over the connection union. The female coupling member can comprise a separate sleeve which is compressed over the connection union by the electromagnetic metal forming operation. Alternatively, the female coupling member can comprise a terminal end of one of the first and second components which includes a longitudinally extending recess which forms an outer circumferentially extending sleeve which is compressed over the connection union by the electromagnetic metal forming operation. In several embodiments, the first and second components are butted together, and each butted end of the first and second components includes at least one circumferentially extending ridge, around which the female coupling member is deformed during the electromagnetic metal forming operation to form an undercut in the female coupling member. In disclosed embodiments, the first component comprises the shaft of an ultrasonic waveguide or blade and the second component comprises a distal tip end of the ultrasonic waveguide such as an end-effector.

23 Claims, 3 Drawing Sheets

ATTACHMENTS OF COMPONENTS OF ULTRASONIC BLADES OR WAVEGUIDES

BACKGROUND OF THE INVENTION

1. Field of the Invention

The present invention relates generally to attachments of, and a method of attaching, any two components of ultrasonic blades or waveguides, and more particularly pertains to attachments, and a method of attaching, of ultrasonic blades or waveguides to blade tips of ultrasonic surgical instruments.

Typical prior art ultrasonic blades or waveguides are produced from one piece of titanium. Some ultrasonic blades or waveguides of ultrasonic surgical instruments, such as the LCS/CS (Laparosonic® Coagulating Shears/Coagulating Shears) blade and certain reusable blades, are produced with a titanium tip that is threaded into an aluminum shaft. This threaded attachment requires threaded components which preclude any simple and low cost manufacturing method of producing the titanium tips except by machining them in a relatively expensive machining operation. Such ultrasonic waveguides or blades are expensive to manufacture when they require machining operations to produce threaded connections.

The present invention relates generally to attachments of any two components of ultrasonic waveguides or blades, such as attachments of ultrasonic waveguides or blades to blade tips such as end-effectors, and a method of attachment thereof, which extend the possible geometries of the ultrasonic waveguides or blades while reducing their manufacturing costs and material waste.

2. Discussion of the Prior Art

Ultrasonic waveguides are utilized in many different technical fields, such as in ultrasonic medical instruments, including both hollow core and solid core instruments, which are well known in the art and are used for the safe and effective treatment of many medical conditions. Ultrasonic instruments, and particularly solid core ultrasonic instruments, are advantageous because they may be used to cut and/or coagulate organic tissue using energy in the form of mechanical vibrations at ultrasonic frequencies transmitted to a surgical end-effector. Ultrasonic vibrations, when transmitted to organic tissue at suitable energy levels using a suitable end-effector, may be used to cut, dissect, or cauterize tissue. Ultrasonic instruments utilizing solid core technology are particularly advantageous because of the amount of ultrasonic energy that may be transmitted from the ultrasonic transducer through an ultrasonic waveguide (also known as a blade) to the surgical end-effector. Such instruments are particularly well suited for use in minimally invasive procedures, such as endoscopic or laparoscopic procedures, wherein the end-effector is passed through a trocar to reach the surgical site.

Ultrasonic surgical instruments and devices typically comprise an ultrasonic transducer which converts an electrical signal to oscillatory motion, an ultrasonic waveguide, and an end-effector which amplifies this motion and applies it to tissue being operated on. Ultrasonic vibration is induced in the surgical end-effector, for example, by electrically exciting a transducer which may be constructed of one or more piezoelectric or magnetostrictive elements in the instrument handpiece. Vibrations generated by the transducer section are transmitted to the surgical end-effector via an ultrasonic waveguide or blade extending from the transducer section to the surgical-end effector.

The ultrasonic waveguide or blade can be formed as a solid core shaft which is machined from a monolithic piece of a titanium or aluminum alloy or any other suitable metal, or the device can be constructed with multiple parts, wherein the multiple parts are joined at antinodes, which are points of low vibrational stress, with joints extending perpendicular to the longitudinal axis of the device. In the prior art, the waveguide or blade can be formed integral with a blade tip or end-effector, or the blade tip or end-effector can be attached thereto with a threaded coupling.

SUMMARY OF THE INVENTION

Accordingly, it is a primary object of the present invention to provide attachments of, and a method of attaching, components of ultrasonic waveguides or blades, such as to blade tips with a joint or attachment design between the shaft of the waveguide or blade and the blade tip which can be easily assembled together without a threaded connection.

A further object of the subject invention is the provision of inexpensive attachments of, and methods to attach, the shaft of a waveguide or blade to a waveguide tip in an ultrasonic instrument. The attachments and methods connect components of the ultrasonic waveguide, such an ultrasonic surgical blade tip to the shaft of a waveguide or blade which is transmitting ultrasonic energy. The connection method utilizes two or more components which are secured together with the use of metal electroforming technology. The present invention reduces the need for expensive machined threaded connections by utilizing a simple design to connect together two components of an ultrasonic waveguide or blade.

The design of the present invention provides two main features to maintain the blade tip and the shaft of the waveguide or blade centered relative to one another and to tightly secure the two components together during ultrasonic activation. These features are functionally equivalent to threaded connections, but are easier to manufacture and less expensive than threaded connections. The two components, the waveguide or blade shaft and the blade tip, can be secured together by a radial compression fit between the components, or secured together by a ring or sleeve fitted over the connection union/joint between the two parts, wherein the ring or sleeve is circumferentially shrunk down and compressed over the connection union/joint by an electromagnetic metal forming process.

A unique advantage of the present invention is an increase in manufacturing and design flexibility because the components do not need machined threads to facilitate the connection, allowing the components to be produced in a simpler fashion, such as by stamping or forging.

In accordance with the teaching herein, the present invention provides a connection union and method for securing together first and second components of an ultrasonic waveguide or blade. The first and second components of the ultrasonic waveguide or blade are formed as complementary components which engage each other with a complementary fitting. Then a compressed fit over the connection union is formed by an electromagnetic metal forming operation which compressively deforms a female coupling member over the connection union.

In greater detail, the female coupling member can comprise a separate sleeve which is compressed over the connection union by the electromagnetic metal forming operation. Alternatively, the female coupling member can comprise a terminal end of one of the first and second components which includes a longitudinally extending recess which forms an outer circumferentially extending sleeve which is compressed over the connection union by the electromagnetic metal forming operation.

In several embodiments, the first and second components are butted together, and each butted end of the first and second components includes at least one circumferentially extending ridge, around which the female coupling member is deformed during the electromagnetic metal forming operation to form an undercut in the female coupling member.

In several embodiments, one of the first and second components comprises a projecting male terminal end, and the other of the first and second components comprises a complementary female terminal end which forms the complementary fitting with the male terminal end. The complementary fitting can be formed by male and female components forming a conical shaped fitting, a frusto-conical shaped fitting, or a cylindrical shaped fitting.

In one embodiment, the complementary fitting is formed by two identical and complementary sandwich half components which face each other along a plane extending along the longitudinal axis of the connection union. Each of the first and second components includes one half of at least one circumferentially extending ridge, around which the female coupling member is deformed around during the electromagnetic metal forming operation to form an undercut in the female coupling member.

In disclosed embodiments, the first component comprises the shaft of an ultrasonic waveguide or blade and the second component comprises a distal tip end of the ultrasonic waveguide such as an end-effector.

BRIEF DESCRIPTION OF THE DRAWINGS

The foregoing objects and advantages of the present invention for attachments of, and a method of attaching, components of ultrasonic waveguides or blades may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
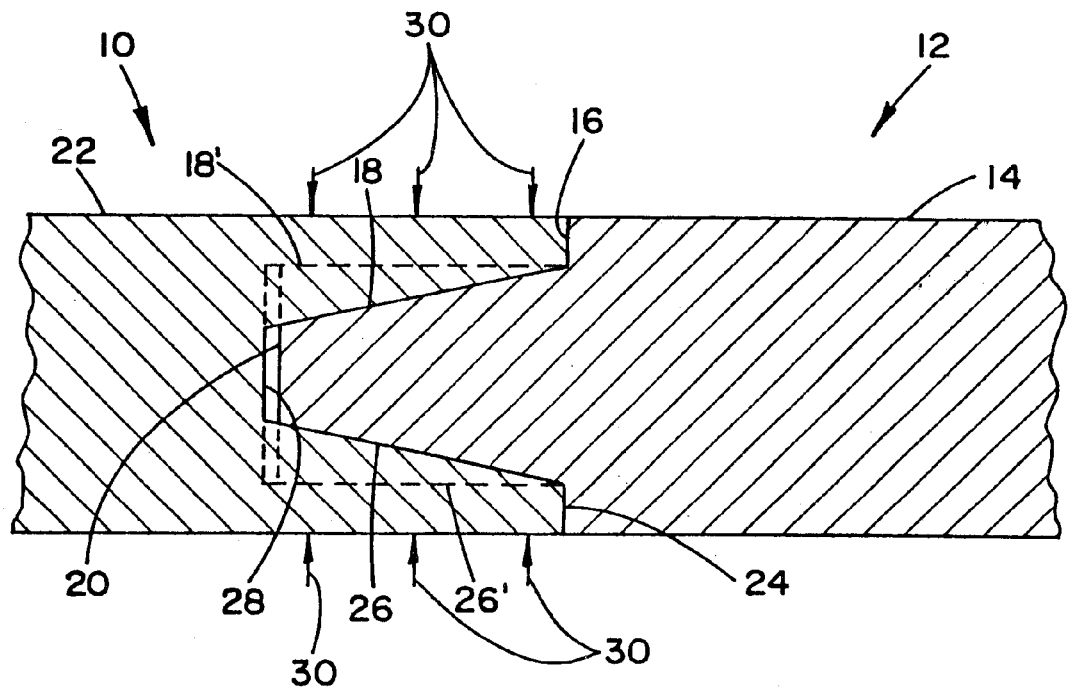
FIG. 1 illustrates a first embodiment of the present invention for a compression attachment of a shaft of an ultrasonic waveguide or blade to a blade tip or end-effector.

Referring to the drawings in detail, FIG. 1 illustrates a first embodiment of the present invention wherein a compression attachment is formed between the shaft 10 of an ultrasonic waveguide or blade to a blade tip 12, which can be an end-effector, of an ultrasonic surgical instrument. The blade tip 12 comprises a generally cylindrical body 14 having an annular shoulder 16 and a projecting frusto-conical joint member 18 extending coaxially therefrom and terminating at an end 20. The shaft 10 of the ultrasonic waveguide or blade comprises a generally cylindrical body 22 having an annular shoulder 24 at the very end thereof, and an internal concave frusto-conical cavity 26 which has a shape corresponding to that of the frusto-conical member 18 and terminates at an end 28.

The connection of FIG. 1 establishes a positive surface contact and connection between the two frusto-conical members 18 and 26 to efficiently transfer ultrasonic energy therebetween. This positive surface connection is completed by an operation of an electromagnetic metal forming process which compresses, along radial arrows 30, the frusto-conical cavity 26 around and against the frusto-conical projecting member 18 to compressively join the two members together. The annular shoulders 16–24 and ends 20–28 also preferably contact and are compressed against each other to transfer ultrasonic energy therebetween.

In this embodiment, female coupling member 10 comprises a terminal end which includes a longitudinally extending frusto-conical recess which forms an outer, circumferentially-extending sleeve which is compressed over the connection union by the electromagnetic metal forming operation.

The illustrated embodiment has the frusto-conical projection on the blade tip 12 and the frusto-conical cavity on the shaft 22 of the ultrasonic waveguide, and complementary embodiments would include the frusto-conical cavity on the blade tip 12 and the frusto-conical projection on the shaft 22 of the ultrasonic waveguide.

In general, the embodiments of connection unions disclosed herein can be formed between any of the components of an acoustic waveguide or blade, and to the extent that the components include different complementary shapes, either component might include either one or the other of the different complementary shapes.

FIG. 1 illustrates in phantom an alternative embodiment having a cylindrical shaped projecting member 18' and a cylindrical shaped cavity 26' which has a shape corresponding to that of member 18'. An advantage of this embodiment is that the compression of the electromagnetic forming process does not place any longitudinal forces on the connection joint tending to cause a separation of the connection joint members.

Figure 2:
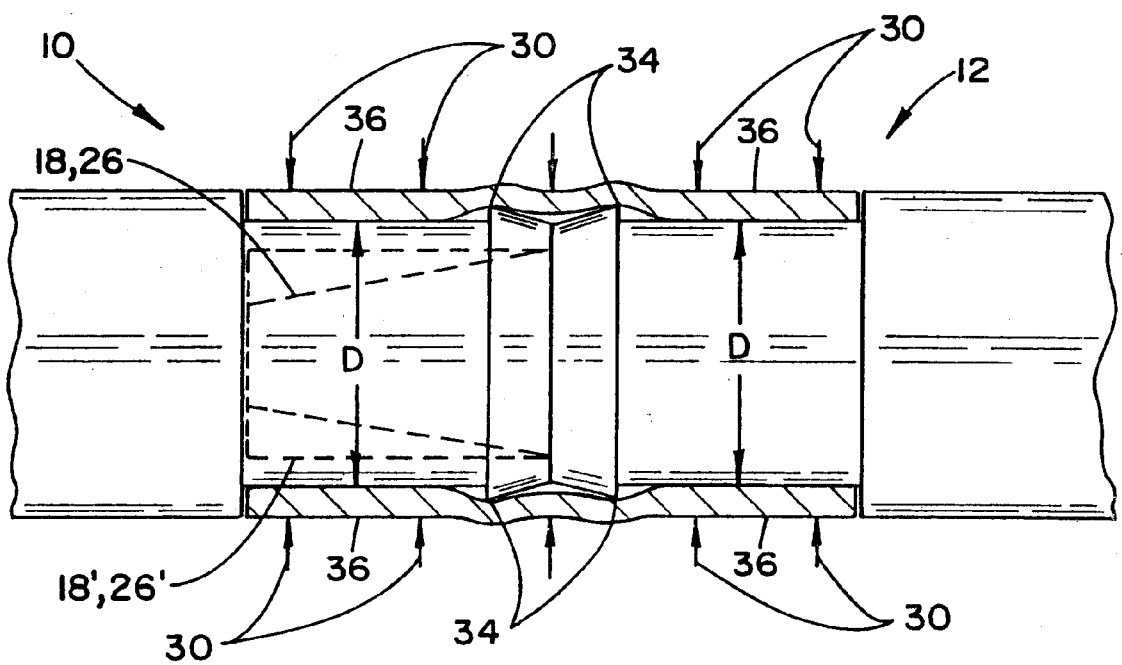
FIG. 2 illustrates a second embodiment of the present invention for a compression attachment of a shaft of an ultrasonic waveguide or blade to a blade tip, wherein the shaft of the waveguide or blade and the blade tip are substantially identical at their ends and are positioned butted end to end, and are secured together by a ring or sleeve as illustrated in FIGS. 4 and 5 fitted over the union joint between the two parts which is shrunk down and compressed over the connection union/joint by an electromagnetic metal forming process.

FIG. 2 illustrates a second embodiment wherein each component, the ultrasonic waveguide or blade 10 and the blade tip 12, defines an annular barbed rib 34 extending circumferentially therearound such that, with the help of a third component—a metallic ring or sleeve 36—it sustains a firm mount by creating an undercut with the ring or sleeve 36. The metallic ring or sleeve 36 can be formed of any suitable metal, with aluminum being one suitable metal.

The embodiment of FIG. 2 can also be combined with the structure of the embodiments of FIG. 1, as illustrated in phantom in FIG. 2, to assist in centering and connecting the components 10 and 12. Each of the waveguide or blade 10 and the blade tip 12 includes a reduced diameter D end section to accommodate the positioning of the ring or sleeve 36 thereon.

The use of the electromagnetic metal forming process as the last step in the construction of the embodiment of FIG. 2 enables the ring or sleeve 36 to shrink down over and compress the joint of the shaft of the waveguide or blade and the blade tip, similar to shrink tubing used in electrical connections, thus enabling an easy assembly with no post assembly movement of the parts relative to each other. The barbed ribs 34 function as an undercut against the deformed ring 36, thus preventing a separation of the connection joint.

Figure 3:
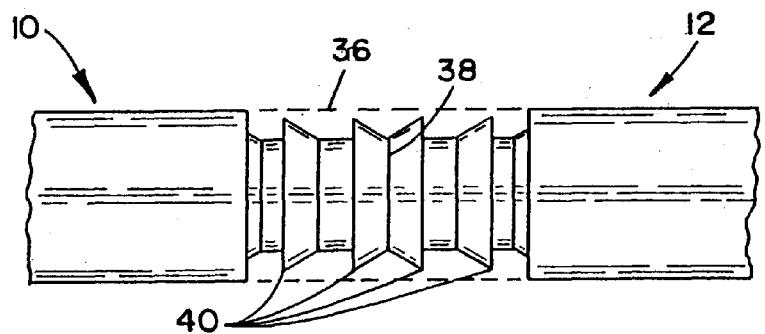
FIG. 3 illustrates a third embodiment wherein two substantially identical (at their ends) joint members are positioned butted end to end, and each joint member includes a plurality of circumferentially extending undercut ridges, and the two components are ready to be secured together by an aluminum ring or sleeve as illustrated in FIGS. 4 and 5 which is then electromagnetic metal formed and compressed around the connection union/joint pursuant to the present invention.
Figure 4:
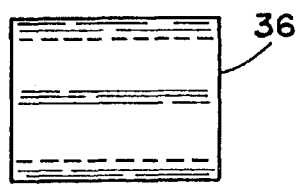
FIGS. 4 and 5 are respectively front elevation and side views of a metallic ring or sleeve which is designed to be electromagnetic metal formed onto and around the connection union/joints of the three designs of respectively FIGS. 2, 3, 6 and 7.
Figure 5:
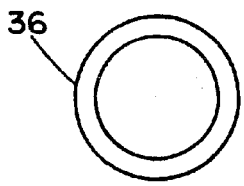

FIG. 3 illustrates a third embodiment of a design for an electroform joint wherein two substantially identical joint members 10, 12 are positioned butted end to end at 38, and each joint member includes a plurality of circumferentially extending undercut ridges 40, and the two components are ready to be secured together by a metallic ring or sleeve 36 as illustrated in FIGS. 4 and 5 which is electromagnetic metal formed over and around the connection union/joint pursuant to the present invention.

FIGS. 4 and 5 are respectively front elevation and side views of a metallic ring or sleeve 36 which is designed to be electromagnetically formed onto and around the connection union/joints of the three designs of respectively FIGS. 2, 3, 6 and 7.

Figure 6:
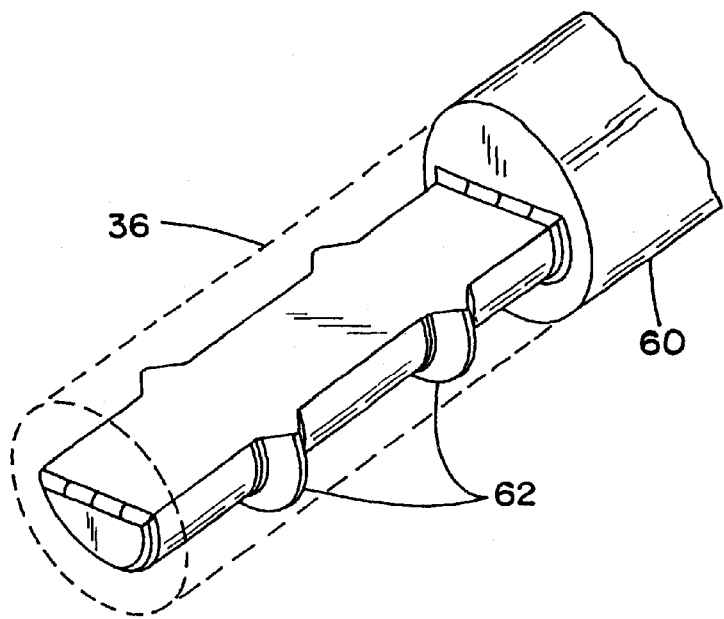
FIG. 6 is a perspective view of a sandwich joint design wherein two substantially identical (at their ends) and complementary sandwich members are designed to be sandwiched one on top of the other, and then secured together by an a metallic or sleeve as illustrated in FIGS. 4 and 5 which is electromagnetic metal formed and compressed around the connection union/joint formed between the complementary sandwich members.

FIG. 6 is a perspective view of a sandwich joint design wherein two identical and complementary sandwich members 60, only one of which is shown in FIG. 6, are designed to be sandwiched one on top of the other. The two identical and complementary sandwich half components 60,60 face each other along a plane extending along the longitudinal axis of the connection union. The two components are then secured together by a metallic ring or sleeve 36, such as illustrated in FIGS. 4 and 5, which is electromagnetic metal formed and compressed around the connection union/joint formed between the complementary sandwich members 60,60. Each component 60 also includes one half of a plurality of circumferentially extending undercut ridges 62 which are embedded into the metal ring or sleeve 36 during the metal forming process.

Figure 7:
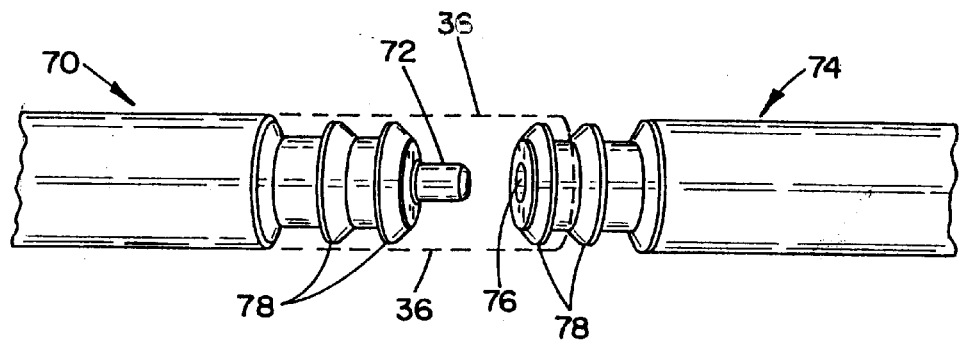
FIG. 7 illustrates a perspective view of a first component having a male post member and a second component having a female recessed member which form a connection union/joint which is secured together by a ring or sleeve as illustrated in FIGS. 4 and 5 which is metal formed and compressed therearound. The male post member and the female recessed member assist in longitudinally aligning the two components, and each component also includes a plurality of circumferentially extending undercut ridges which are embedded into the metallic ring or sleeve during the electromagnetic metal forming process.

FIG. 7 illustrates a perspective view of a first component 70 having a male post member 72 and a second component 74 having a female recess 76 which form a connection union/joint which is secured together by a ring or sleeve such as illustrated in FIGS. 4 and 5 which is metal formed and compressed therearound. The male post member 72 and the female recessed member 76 assist in longitudinally aligning the two components 70,74, and each component also includes a plurality of circumferentially extending undercut ridges 78 which are embedded into the metal ring or sleeve during the electromagnetic metal forming process.

Figure 8:
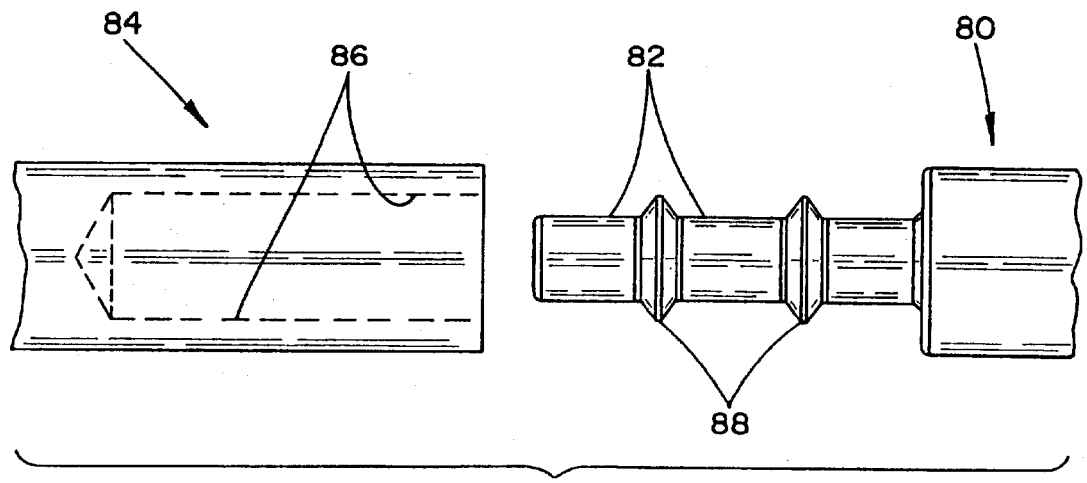
FIG. 8 illustrates a further embodiment of a male component and a female component of a two piece connection union/joint which are designed to be interfitted and then compressed together by an electromagnetic metal forming process without a sleeve compressed therearound. The male component also includes a plurality of circumferentially extending undercut ridges, and the hollow sleeve of the female component is designed to be compressed and deform around the circumferentially extending undercut ridges of the male component during the compression electromagnetic metal forming process.

FIG. 8 illustrates a further embodiment of a male component 80 having a substantially cylindrical projection 82 and a female component 84 having a substantially cylindrical recess 86 of a two piece connection union/joint which are designed to be interfitted and then compressed together by an electromagnetic metal forming process without a sleeve 36 compressed therearound. The male component 80 also includes a plurality of circumferentially extending undercut ridges 88 on the cylindrical projection 82, and the hollow sleeve 86 of the female component is designed to be compressed and deform around the circumferentially extending undercut ridges 88 of the male component during the compression electromagnetic metal forming process.

An important enabling feature in an ultrasonic waveguide is the placement of the joint/connection at a nodal point of the ultrasonic blade/scalpel, which has the least stress and therefore reduces risk of failure.

Prior to the electromagnetic metal forming process, the connection components can be annealed to a TO condition to lower the tensile yield strength thereof for the metal forming process. After the electromagnetic metal forming process, the connection components can be heat treated back to T6 to increase the tensile strength thereof, wherein TO and T6 conditions are common heat treatment conditions for aluminum.

While several embodiments and variations of the present invention for attachments of components of ultrasonic waveguides or blades are described in detail herein, it should be apparent that the disclosure and teachings of the present invention will suggest many alternative designs to those skilled in the art.

What is claimed is:

1. A connection union for an ultrasound therapy system comprising:

a first component and a second component of the ultrasound therapy system are complementary components, which engage each other with a complementary fitting, a compression fitting over the connection union is formed by a deformed female coupling member which is deformed around the complementary fitting of the first and second components by an electromagnetic metal forming operation which compressively deforms the female coupling member over the complementary fitting of the first and second components of the connection union.

2. The connection union of claim 1, wherein the female coupling member comprises a separate sleeve which is compressed over the connection union by the electromagnetic metal forming operation.

3. The connection union of claim 1, wherein the female coupling member comprises a terminal end of one of the first and second components which includes a longitudinally extending recess which forms an outer circumferentially extending sleeve which is compressed over the connection union by the electromagnetic metal forming operation.

4. The connection union of claim 1, wherein the ends of the first and second components are butted together, and each butted end of the first and second components includes at least one circumferentially extending ridge, around which the female coupling member is deformed during the electromagnetic metal forming operation to form an undercut in the female coupling member.

5. The connection union of claim 4, wherein one of the first and second components comprises a projecting male terminal end, and the other of the first and second components comprises a complementary female terminal end which forms the complementary fitting with the male terminal end.

6. The connection union of claim 1, wherein one of the first and second components comprises a projecting male terminal end, and the other of the first and second components comprises a complementary female terminal end which forms the complementary fitting with the male terminal end.

7. The connection union of claim 6, wherein the complementary fitting is formed by male and female components forming a conical shaped fitting.

8. The connection union of claim 6, wherein the complementary fitting is formed by male and female components forming a frusto-conical shaped fitting.

9. The connection union of claim 6, wherein the complementary fitting is formed by male and female components forming a cylindrical shaped fitting.

10. The connection union of claim 1, wherein the complementary fitting is formed by two identical and complementary sandwich half components which face each other along a plane extending along the longitudinal axis of the connection union.

11. The connection union of claim 10, wherein each of the first and second components includes one half of at least one circumferentially extending ridge, around which the female coupling member is deformed during the electromagnetic metal forming operation to form an undercut in the female coupling member.

12. The connection union of claim 1, wherein the first component comprises an ultrasonic waveguide or blade and the second component comprises a distal tip end of the ultrasonic waveguide.

13. A connection method for an ultrasound therapy system comprising:
    forming a first component and a second component of the ultrasound therapy system as complementary components which engage each other with a complementary fitting in a connection union,
    forming a compression fitting over the connection union by an electromagnetic metal forming operation which compressively deforms a female coupling member over the complementary first and second complementary components of the connection union.

14. The connection method of claim 13, including forming the female coupling member as a separate sleeve which is compressed over the connection union by the electromagnetic metal forming operation.

15. The connection method of claim 13, including forming the female coupling member at a terminal end of one of the first and second components by forming a longitudinally extending recess therein, which forms an outer circumferentially extending sleeve which is compressed over the connection union by the electromagnetic metal forming operation.

16. The connection method of claim 13, including butting the ends of the first and second components together, and forming each butted end of the first and second components with at least one circumferentially extending ridge, around which the female coupling member is deformed during the electromagnetic metal forming operation to form an undercut in the female coupling member.

17. The connection method of claim 16, including forming one of the first and second components with a projecting male terminal end, and forming the other of the first and second components with a complementary female terminal end which forms the complementary fitting with the male terminal end.

18. The connection method of claim 13, including forming one of the first and second components with a projecting male terminal end, and forming the other of the first and second components with a complementary female terminal end which forms the complementary fitting with the male terminal end.

19. The connection method of claim 18, including forming the complementary fitting by male and female components which form a conical shaped fitting.

20. The connection method of claim 18, including forming the complementary fitting by male and female components which form a frusto-conical shaped fitting.

21. The connection method of claim 18, including forming the complementary fitting by male and female components which form a cylindrical shaped fitting.

22. The connection method of claim 13, including forming the complementary fitting by two identical and complementary sandwich half components which face each other along a plane extending along the longitudinal axis of the connection union.

23. The connection method of claim 22, including forming each of the first and second components with one half of at least one circumferentially extending ridge, around which the female coupling member is deformed during the electromagnetic metal forming operation to form an undercut in the female coupling member.

* * * * *